US006552243B2

(12) United States Patent
Allison et al.

(10) Patent No.: US 6,552,243 B2
(45) Date of Patent: Apr. 22, 2003

(54) CATALYST AND PROCESS FOR AROMATIC HYDROCARBONS PRODUCTION FROM METHANE

(75) Inventors: Joe D. Allison, Ponca City, OK (US); Stephan Basso, Strasbourg (FR); Marc LeDoux, Strasbourg (FR); Cuong Pham-Huu, Strasbourg (FR); Harold A. Wright, Ponca City, OK (US)

(73) Assignee: Conoco Phillips Company, Houston, TX (US)

( * ) Notice: Subject to any disclaimer, the term of this patent is extended or adjusted under 35 U.S.C. 154(b) by 0 days.

(21) Appl. No.: 09/916,469

(22) Filed: Jul. 27, 2001

(65) Prior Publication Data

US 2002/0072642 A1 Jun. 13, 2002

Related U.S. Application Data

(60) Provisional application No. 60/221,082, filed on Jul. 27, 2000.

(51) Int. Cl.⁷ .............................. C07C 2/08; C07C 2/52
(52) U.S. Cl. ...................... 585/943; 585/417; 585/418; 585/420; 585/906
(58) Field of Search .............................. 585/943, 417, 585/418, 420, 906

(56) References Cited

U.S. PATENT DOCUMENTS

| | | | |
|---|---|---|---|
| 4,727,206 A | 2/1988 | Clayson et al. | 585/415 |
| 5,026,937 A | 6/1991 | Bricker | 585/415 |
| 5,672,796 A | 9/1997 | Froment et al. | 585/419 |
| 5,936,135 A | 8/1999 | Choudhary et al. | 585/418 |

OTHER PUBLICATIONS

Yide Xu et al, "Methane Activation without using oxidants over Mo/HZSM–5 zeolite catalysts", Catalysis Letters 30, 135–149 (1995).

Laiyuan Chen, et al, "Dehydro–oligomerization of Methane to Ethylene and Aromatics over Molybdenum/HZSM–5 Catalyst", Journal of Catalysis 157, 190–200 (1995).

F. Solymosi, et al, "Conversion of methane to benzene over $Mo_2C$ and $Mo_2C$/ZSM–5 catalysts", Catalysis Letters 39, 157–161, (1996).

Bert M. Weckhuysen et al, "Characterization of surface carbon formed during the conversion of methane to benzene over Mo/H–ZSM–5 catalysts", Catalysis Letters 52, 31–36 (1998).

Linsheng Wang, et al, "Activity and stability enhancement of Mo/HZSM–5–based catalyst for methane non–oxidative transformation to aromatics and $C_2$ hydrocarbons: Effect of additives and pretreatment conditions", Applied Catalysis A: General 152, 173–182, (1997).

Dingjum Wang, et al, "Characterization of a Mo/ZSM–5 Catalyst for the Conversion of Methane to Benzene", Journal of Catalysis 169, 347–358, (1997).

(List continued on next page.)

Primary Examiner—Thuan D. Dang
(74) Attorney, Agent, or Firm—Conley, Rose & Tayon PC

(57) ABSTRACT

A molybdenum-loaded crystalline aluminosilicate molecular sieve that exhibits the MFI crystal structure and has a silica-to-alumina ratio of about 50:1 is useful for aromatizing a hydrocarbon feed stream. The crystalline aluminosilicate preferably has an external surface acidity selectively passivated by means of an amorphous silica layer. A process for the aromatization of methane comprises a one- or multi-step process that contacts a feed stream comprising at least methane with a catalyst composition comprising the preferred molecular sieve, at hydrocarbon conversion conditions that include a temperature of 600–800° C., a pressure of less than 5 atmospheres absolute and a Weight Hourly Space Velocity (WHSV) of 0.1–10 $h^{-1}$, with the external surface acidity of the crystalline aluminosilicate preferably selectively passivated by an amorphous silica layer. $C_6$-plus aromatic hydrocarbons are preferably recovered from the process by means of an intermediate separation step.

23 Claims, 5 Drawing Sheets

OTHER PUBLICATIONS

Bert M. Weckhuysen, et al, "Conversion of Methane to Benzene over Transition Metal Ion ZSM–5 Zeolites", Journal of Catalysis 174, 338–346 (1998).

Liliana B. Pierella, et al, "Selective Ethane Conversion Into Aromatic Hydrocarbons over Zn–ZSM–11 Zeolite", React. Kinet. Catal. Lett. vol. 63, No. 2, 271–278, (1998).

L. Guczi, et al, "One Step" Methan Conversion Under Non Oxidative Condition Over Pt–Co/NaY Catalysts at Low Temperature, Natural Gas Conversion V, Studies in Surface Science and Catalysis, vol. 119, 295–300, (1998).

Xie Mao–song et al, "The Oxidative Coupling of Methane and the Aromatization of Methane Without Using Oxidants", Natural Gas Conversion V, Studies in Surface Science and Catalysis, vol. 119, 319–324, (1998).

Richard W. Borry III et al, "Non–Oxidative catalytic conversion of methane with continuous hydrogen removal", Natural Gas Conversion V, Studies in Surface Science and Catalysis, vol. 119, 403–410 (1998).

Yuan Lu et al, "Methane aromatization in the absence of an added oxidant and the bench scale reaction test", Catalysis Letters 62, 215–220, (1999).

Shuang Li et al, "The function of Cu(II)ions in the Mo/Cu-H–ZSM–5 catalyst for methane conversion under non–oxidative condition" Applied Catalysis A: General 187, 199–206, (1999).

Yide Xu, Liwu Lin, "Recent advances in methane dehydro–aromatization over transition metal ion–modified zeolite cataysts under non–oxidative conditions", Applied catalysis A: General 188, 53–67, (1999).

Jun Shu et al, "Bifunctional Behavior of Mo/HZSM–5 Catalysts in Methane Aromatization", Ind. Eng. Chem. Res. 38, 3860–3867, (1999).

She–Tin Wong et al, "Methane Conversion Over Mo/HZSM–5 Catalysts Without Adding $O_2$—A Reaction on Remotely Separated Active Sites" Journal of Natural Gas Chemistry Vo. 8 No. 4, 267–279, (1999).

Shetian Liu et al, "Bifunctional Catalysis of Mo/HZSM–5 in the Dehydroaromatization of Methane to Benzene and Naphthalene XAFS/TG/DTA/MASS/FTIR Characterization and Supporting Effects", Journal of Catalysis 181, 175–188, (1999).

B.M. Weckhuysen et al, "Direct Conversion of Methane To Aromatics Over Transition Metel Ion–Loaded H–ZSM–5 Zeolites", $12^{th}$ International Zeolite Conference Materials Research Society, 1381–1388, (1999).

PCT International Search Report for International Application No. PCT/US01/23769 dated Jun. 3, 2002 (p. 6).

CATALYST AND PROCESS FOR AROMATIC HYDROCARBONS PRODUCTION FROM METHANE

CROSS-REFERENCE TO RELATED APPLICATIONS

The present application claims benefit of priority from U.S. application Serial No. 60/221,082, filed Jul. 27, 2000 and entitled "Catalyst and process for aromatic hydrocarbons production from methane," which is incorporated herein by reference.

STATEMENT REGARDING FEDERALLY SPONSORED RESEARCH OR DEVELOPMENT

Not applicable.

FIELD OF THE INVENTION

The present invention relates to a catalyst preparation and hydrocarbon conversion process used for upgrading natural gas into more valuable hydrocarbons. The invention specifically relates to a process for the conversion of hydrocarbon feedstock containing a major proportion of methane into liquids rich in aromatic hydrocarbons such as benzene, toluene, xylene and naphthalene. The scope of the invention preferably comprises the non-oxidative aromatization of methane using a crystalline aluminosilicate molecular sieve catalyst exhibiting a high conversion and a high selectivity to such aromatic hydrocarbons. Such crystalline aluminosilicate molecular sieve catalysts preferably contain molybdenum carbide or oxycarbide, have high stability, and are suitable for multiple regeneration.

BACKGROUND OF THE INVENTION

There has been recognition in the prior art that it is desirable to convert methane into a higher molecular weight hydrocarbon. For instance, it is known that it is normally commercially unfeasible to transport methane produced with crude oil or natural gas from a well site to a distant location for consumption as fuel. Often the transportation problems relate to the extremely low temperatures needed to liquefy methane or to liquefy a gas mixture containing large amounts of methane. It is normally very costly to separate other light hydrocarbons such as ethane from methane and it is undesirable to admix methane with other hydrocarbons prior to transport. The result has been that large amounts of methane are essentially disposed of in a wasteful manner as by flaring without utilization of the hydrocarbonaceous nature of the methane.

U.S. Pat. No. 4,567,311 issued to L. DeVires et al. teaches the recognition of the general problem of methane utilization and also for its presentation of a process for the upgrading of methane using a specific silicon-containing catalyst. This reference provides an excellent discussion of the problems involved with methane utilization and provides a summary of the prior art relating to other methods of converting methane to ethylene or other $C_{2+}$ hydrocarbons.

U.S. Pat. No. 4,565,897 issued to B. R. Gane et al. teaches the conversion of $C_{2+}$ hydrocarbons using a catalyst comprising a ZSM-5 variety zeolite and gallium.

U.S. Pat. No. 4,654,455 issued to T. Chao teaches the preparation and use of a catalyst that comprises a phosphorous-containing alumina, a gallium component and a crystalline aluminosilicate such as a ZSM zeolite. The reference is directed to the conversion of $C_2$–$C_5$ aliphatic hydrocarbons to aromatic hydrocarbons.

U.S. Pat. No. 4,727,206 issued to D. M. Clayson et al. teaches the conversion of methane to aromatic hydrocarbons at 600–800 degrees C. using a catalyst that comprises an aluminosilicate such as a ZSM-5 variety zeolite, which has been exchanged or loaded with (i) gallium or a compound thereof and (ii) a metal or a compound thereof from Group VIIB of the Periodic Table. The preferred group VIIB metal is rhenium. This reference also teaches, at line 39–41 of column 1, that the feedstream may contain at least 50 percent and preferably at least 70 weight percent methane. The three examples all specify the aromatization of methane by contacting the catalyst with methane. Dantsin and Suslick, in an article entitled "Sonochemical Preparation of a Nanostructured Bifunctional Catalyst", in the Journal of the American Chemical Society, Communications to the Editor, teach preparation of "eggshell catalysts" for the dehydroaromatization of methane to benzene, where the outer surface of the support holds nanometer sized catalyst particles. The catalyst of this reference has essentially all of the active metal on the outer surface of a ZSM-5 support relative to the pores.

SUMMARY OF THE INVENTION

It has been found that methane can be aromatized using a catalyst composition comprising a molybdenum-loaded crystalline aluminosilicate molecular sieve exhibiting the MFI crystal structure. The process of the invention preferably operates at reaction temperatures of 600–800° C. in the absence of oxygen.

Accordingly, the present invention comprises preparation of a molybdenum-loaded crystalline aluminosilicate molecular sieve that exhibits the MFI crystal structure and has a silica-to-alumina ratio of about 50:1, said crystalline aluminosilicate preferably having the external surface acidity selectively passivated by means of an amorphous silica layer.

In another aspect, the invention comprises a one or multi-step process that contacts a feed stream, comprising at least methane, with a catalyst composition comprising a molybdenum-loaded crystalline aluminosilicate molecular sieve that exhibits the MFI crystal structure and has a silica-to-alumina ratio of 50:1, said crystalline aluminosilicate preferably having the external surface acidity selectively passivated by means of an amorphous silica layer, at hydrocarbon conversion conditions that include a temperature of 600–800° C., a pressure of less than 5 atmospheres absolute and a Weight Hourly Space Velocity (WHSV) of 0.1–10 $h^{-1}$, and recovering product $C_6$-plus hydrocarbons by means of an intermediate separation step.

BRIEF DESCRIPTION OF THE DRAWNGS

For a more detailed understanding of the invention reference is made to the accompanying Figures, wherein:

FIG. 1 is a graphical illustration of the influence of the activation process on the catalytic activity of a catalyst in accordance with the present invention, at 700° C. over crystalline aluminosilicate supported molybdenum cluster modified with carbon and oxygen, for (a) activation under $H_2$/n-$C_4H_{10}$ (molar ratio 9:1), (b) activation under $H_2$/$CH_4$ (molar ratio 1:1), and (c) no activation, and depicts the experimental results of Examples 1–3.

FIG. 2 is a graphical illustration of the influence of the deposition method on the catalytic activity of a catalyst in accordance with the present invention, at 700° C. over crystalline aluminosilicate supported molybdenum cluster modified with carbon and oxygen, for catalyst (a) prepared by chemical vapor deposition technique and (b) prepared by incipient wetness technique, and depicts the experimental results of Examples 4 and 5.

Figure 5:
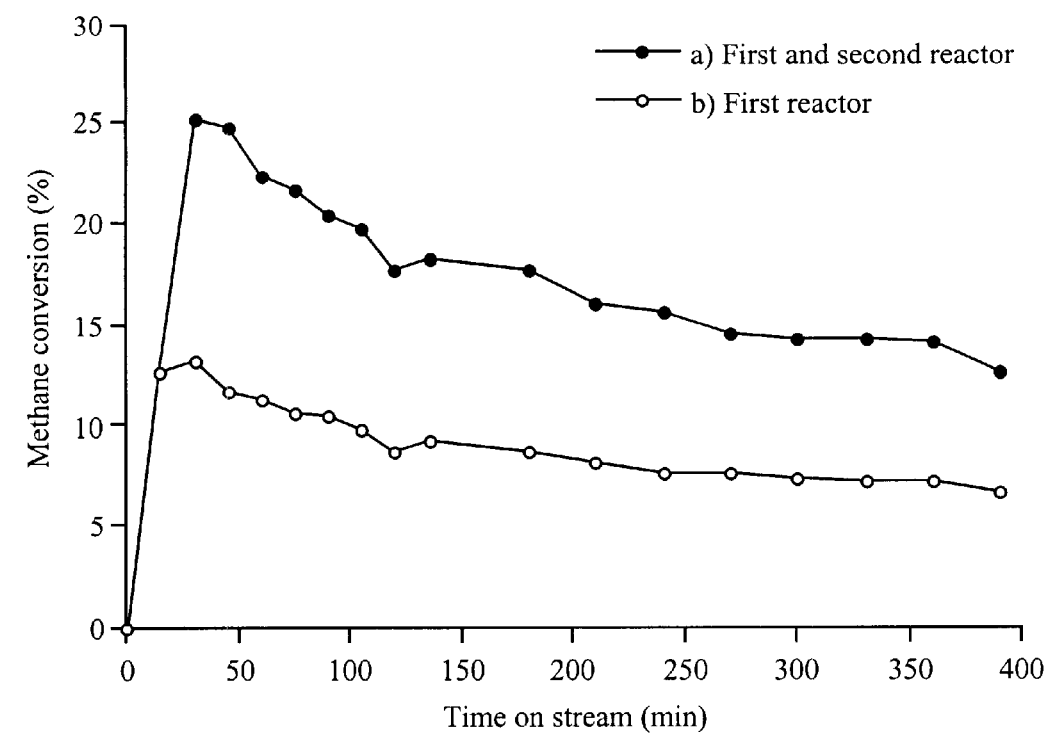
Figure 5:
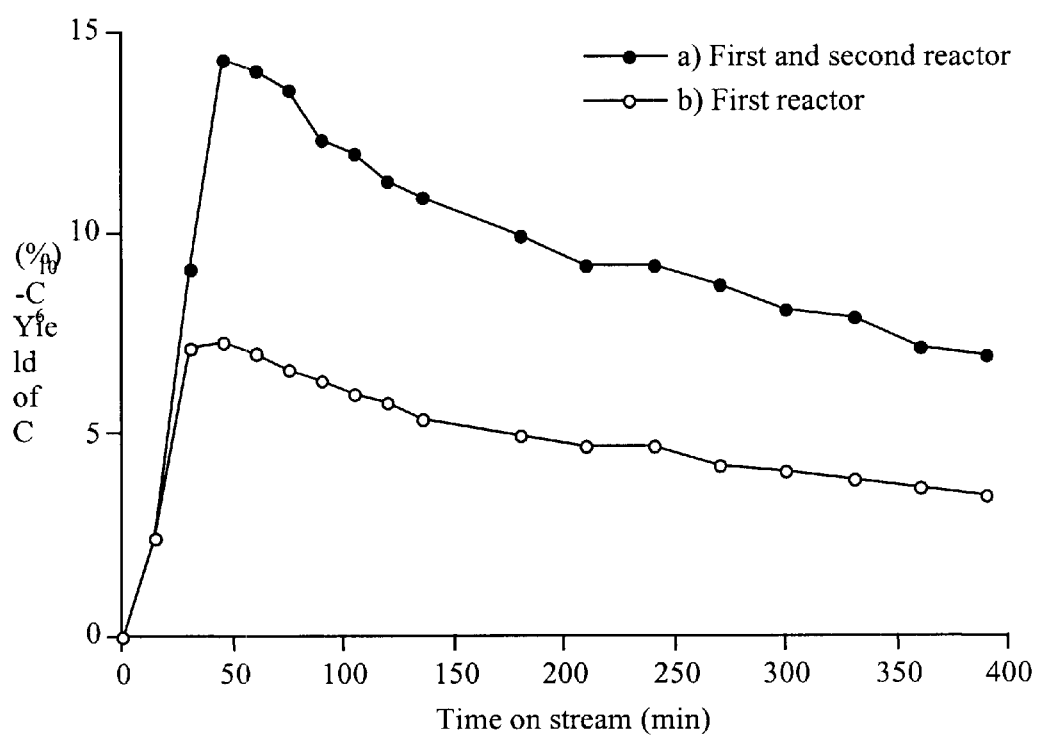

FIG. 5 is a graphical illustration of the influence of cascade reactors using an intermediate alumina membrane in accordance with the present invention, on the yield of $C_6$–$C_{10}$ over crystalline aluminosilicate supported molybdenum cluster modified with carbon and oxygen at 700° C. for (a) first and second (cascade) reactor system and (b) first (single) reactor, and depicts the experimental results of Example 8.

DETAILED DESCRIPTION OF THE INVENTION

The subject invention comprises contacting the methane-containing feed stream with a solid catalyst maintained at reaction conditions in a reaction zone. The feed stream which is useful in the process described herein preferably contains at least methane. The feed stream can be a stream of essentially pure methane although even a pure stream of gas is likely to contain some small amount, up to 0.5 mole percent of impurities. The impurities may be nitrogen or other inorganic species. The feed stream can also contains higher hydrocarbons having chain lengths of up to 4, due to the less than perfect separations used in commercial scale processes. Specific examples of such additional hydrocarbons are ethane, propane, propylene, n-butane, isobutane, n-butenes and isobutene and other compounds as would be known to one of skill in the art. As used herein, it is more preferred that the feed stream contains a molar concentration over 40 percent methane, and it is highly preferred that the feed stream contains 50 mole percent methane.

One embodiment of the invention comprises the presence of hydrogen in the feed stream during the activation of the catalyst. In this embodiment of the invention, it is preferred that the feed stream in the reaction zone contains at least 25 mole percent hydrogen. A highly preferred hydrogen concentration is from about 25 to 75 mole percent. Most preferably, the hydrogen concentration is about 50 mole percent.

In another aspect of the embodiment of the invention, the feed stream may contain $C_2$ to $C_4$ alkanes during the activation of the catalyst. More preferably it is ethane, propane, butane or a mixture of two or more of such saturated hydrocarbons. Most preferably it is butane. It is preferred that the feed stream for such activation be adjusted to contain at least 50 mole percent hydrogen. A highly preferred hydrogen concentration is from about 50 to 90 mole percent. During such activation, the feed stream is brought into contact with the catalyst in a reaction zone at hydrocarbon conversion conditions which include a temperature between about 250° C. and about 650° C., more preferably between about 350° C. and about 550° C. The activation generally takes place at atmospheric pressure, but the pressure may be within the approximate range of about 0.5 bar to 5 bar, more preferably between about 0.5 bar and about 2 bar. The activation is suitably accomplished using a Weight Hourly Space Velocity (WHSV) between about 0.5 h–1 and about 4 h$^{-1}$, and more preferably between about 0.5 and 2 h$^{-1}$.

The methane-containing feed stream used for the aromatization is brought into contact with the catalyst in a reaction zone comprising a single reactor or several separate reactors in series for the multi-step process. Products $C_6$-plus hydrocarbons for the multi-step process are recovered by means of an intermediate separation step. The catalyst within the reactor is maintained as an immobile or fixed bed. However, processes using one or more fluidized beds could also be operated without detrimental effect on the reaction conversion.

The catalytic composition employed in the subject invention may accordingly be characterized as comprising a catalytic composition comprising a crystalline aluminosilicate molecular sieve. This crystalline aluminosilicate eventually having the external surface acidity selectively passivated by means of an amorphous silica layer.

The molecular sieve used in the present invention may be a pentasil crystalline aluminosilicate. "Pentasil" is a term used to describe a class of shape-selective molecular sieve. Of the class of pentasil crystalline aluminosilicates, the preferred aluminosilicates are ZSM-5, ZSM-8, ZSM-11, ZSM-23 and ZSM-35, with ZSM-5 being particularly preferred. The ZSM-5 molecular sieve is a coarse crystalline, three-dimensional, stable structure consisting of two sets of intersecting channels through 10-membered ring windows, one straight (5.3×5.6 A) and the other sinusoïdal (5.1×5.5 A). This aluminosilicate may be represented by the general formula:

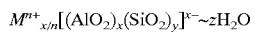

$$M^{n+}{}_{x/n}[(AlO_2)_x(SiO_2)_y]^{x-} \sim zH_2O$$

where M is a cation that is a positively charged ion selected from a metal ion or an organic ion of valence n or hydrogen, x+y is the total number of tetrahedrals per cell, and z is a function of the degree of hydration and varies from 0 to 16.

Metal cations useful in the formation of ZSM-5 molecular sieves include cetious alkali metals or alkaline earth metals. Because of the basic conditions required for crystallization of the aluminosilicate, the source of such a cation usually is a hydroxide, preferably sodium hydroxide. Organic compounds useful in preparing ZSM-5 molecular sieves include alkylammonium cations or precursors such as tetraalkylammonium compounds. Most preferably, it is tetrapropylammonium cations.

The crystalline material can be prepared by mixing a silica source, an alumina source, an alkali metal hydroxide, a nitrogen-containing organic base as template, and water. Preparation of ZSM-5 molecular sieve is described in greater detail in U.S. Pat. Nos. 3,702,886 and Re. 29,948, which are hereby incorporated herein by reference for all purposes.

The preferred ZSM-5 crystalline aluminosilicate used in the present invention has a silica-to-alumina ratio of 50:1.

The methane conversion catalyst used in the aromatization process preferably contains a metal component. The preferred metal component is molybdenum or molybdenum compounds. The final methane conversion catalyst should contain less than 10 wt. percent metal as measured on an elemental analysis basis. It is preferred that the final catalyst contains from about 0.5 to about 4.0 wt. percent total metal component. A highly preferred concentration for molybdenum on the final methane conversion catalyst is from about 0.5 to about 2.0 wt. percent.

Catalytically active metal is deposited onto the crystalline aluminosilicate by means of any of the following methods. The catalytically active metal may be added by the incipient wetness impregnation of a water soluble metal salt, such as the ammonium heptamolybdate. Another suitable method is the direct vaporization of the catalytically active metal, such as molybdenum oxide, onto the crystalline aluminosilicate. Other methods as are known in the art may also be used.

It is preferred that the catalytically active metal is uniformly distributed throughout the entire network of the final methane conversion catalyst rather than merely on the surface of such catalyst.

The crystalline metal-loaded aluminosilicate useful in the aromatization process may preferably be admixed with an amorphous silica matrix depending upon the intended process use. Typically, the surface of the crystalline aluminosilicate is covered with an amorphous silica layer to improve shape selectivity by passivating the external surface of the support which contains acidic sites, coke precursor sites, and non-shape selectivity molybdenum catalyst. The amorphous silica passivating layer has no effect on the accessibility of the pores of the molecular sieve. Amorphous silica layers may be obtained by means of well known techniques as are understood by one skilled in the art. Preferably, said amorphous silica layer is placed on the surface of the crystalline aluminosilicate by means of chemical vapor deposition (CVD) or by means of chemical liquid deposition (CLD) of silicon alkoxides, most preferably tetraethoxysilane. The crystalline aluminosilicate composition that is formed can be separated and recovered by filtration with aqueous washing. Typically, calcination at temperatures ranging from about 350° C. to about 600° C. and preferably from about 450° C. to about 550° C. is necessary to remove organic compounds on the surface of the molecular sieve.

The final methane conversion catalyst can be pelletized and thereafter crushed, and the result sieved to 0.250 to 0.425 mm particles.

One embodiment of the invention may accordingly be characterized as a process for non-oxidative aromatization of methane which comprises passing a feed stream of methane, into a reaction zone in the presence of the above-described catalyst composition at hydrocarbon conversion conditions which include a temperature between about 600° C. and about 800° C., more preferably between about 675° C. and about 750° C. The reaction generally takes place at atmospheric pressure, but the pressure may be within the approximate range of about 0.5 bar to 5 bar, more preferably between about 0.5 bar and about 2 bar. The reaction is suitably accomplished using a Weight Hourly Space Velocity (WHSV) between about 0.1 and about 10 $h^{-1}$, and more preferable between about 0.1 and 4 $h^{-1}$. The process of the invention produces a reaction zone effluent stream comprising methane, hydrogen, and a selectivity to products from $C_6$ to $C_{10}$ preferably greater than about 30%, more preferably greater than 45%, and most preferably greater than 60%.

In another aspect of the embodiment, the invention comprises a multi-step process that comprises passing methane as a feed stream, into at least two reactors in series in the presence of the above-described catalyst composition at hydrocarbon conversion conditions, which include a temperature between about 600° C. and about 800° C., more preferably between about 675° C. and about 750° C. The reaction generally takes place at atmospheric pressure, but the pressure may be within the approximate range of about 0.5 bar to 5 bar, more preferably between about 0.5 bar and about 2 bar. The reaction is suitably accomplished using a Weight Hourly Space Velocity (WHSV) between about 0.1 $h^{-1}$ and about 10 $h^{-1}$, and more preferably between about 0.1 $h^{-1}$ and 4 $h^{-1}$. The present process produces a reaction zone effluent stream comprising methane, hydrogen, and at least a selectivity in products from $C_6$ to $C_{10}$ preferably greater than about 30%, more preferably greater than 45%, and most preferably greater than 60%. In a multi-stage system, at least the $C_6$–$C_{10}$ products are preferably recovered by means of an intermediate separation step, which results in an intermediate stream comprising methane and hydrogen. Removal of the $C_6$ to $C_{10}$ products can be accomplished by passing the reaction zone effluent stream through a cold trap or other suitable device. The cold trap lowers the temperature of the reaction zone effluent stream, thereby causing certain products to condense. The intermediate stream is then passed into the next reaction zone in the presence of the above-described catalyst composition. This prevents the catalyst in the next reactor from coke deposition, which is a typical aspect of the subject process described in the present invention.

In addition to removing the $C_6$ to $C_{10}$ hydrocarbon products between the stages, a preferred system also includes either inter-stage or intra-stage hydrogen removal, or both. In particular, a preferred multi-stage system includes either an organic or organic or inorganic hydrogen selective membrane positioned such that hydrogen in the intermediate stream can pass through the membrane and thereby be separated from the remainder of the intermediate stream. Alternatively or in addition, the reactor wall can include or comprise a hydrogen selective membrane, so that hydrogen can be separated from the system continuously during reaction. It will be understood that other hydrogen removal techniques can be applied between the stages or to the reactor systems. Removal of hydrogen from the stream and/or reactor(s) in this manner will drive the reaction toward completion.

In another aspect, one embodiment of the subject process comprises the recycling of the components of the reaction zone from the product recovery facilities. These products may be recycled individually or in admixture. These recycled products could comprise low molecular weight hydrocarbons. For instance, ethane and ethylene recovered from the intermediate separation step may be recycled by admixture into the methane feed stream. As another embodiment of the present invention, hydrogen produced in the reaction zone, considered also as a valuable product of the process, may be recycled using any of several techniques known to those skilled in the art of hydrocarbon conversion process design. By way of illustration and not limitation, hydrogen may be recovered by the use of membrane separation technology or by the use of adsorptive separation, such as pressure-swing adsorption.

EXAMPLES

General

All percentages are mole % unless otherwise stated. All elemental analyses were done using Inductively Coupled Plasma (ICP) techniques. Powdered X-ray Diffraction patterns were recorded on a Siemens D5000 using Cu-Kα radiation over a range of 2θ values from 5 to 50° in a step-scan mode.

The $NH_4$-ZSM-5 aluminosilicate molecular sieves distributed by Zeolyst International™ under the CBV5524G reference, which has a silica-to-alumina ratio of 50:1, was used in the following examples.

Catalytic runs were carried out in a flow system, using a quartz tubular flow microreactor having an internal diameter of 6 mm and a length of 800 mm, and using 0.5 g of the above-described catalyst composition. Reactant and diluent gases, including hydrogen, helium, methane, and butane, were used without further purification. Gas flows were regulated by mass flow controller (Brooks models 5850TR).

All experiments were carried out isothermally, at atmospheric pressure, under a mixture of methane and helium (molar ratio 1:1) with a Weight Hourly Space Velocity of 0.5 $h^{-1}$, unless otherwise stated. The product distribution was analyzed by on-line gas chromatography with a flame ionization detector. The conversion of methane and the selectivity in the different products were calculated on the basis of the carbon number.

Influence of Activation Process

Catalyst Preparation

In Examples 1–3 below, catalyst was prepared by direct vaporization of $MoO_3$ onto the crystalline aluminosilicate molecular sieve. The amount of molybdenum was kept constant at 3.9 wt. %. Typically, a mechanical mixture of 0.32 g of $MoO_3$ with 5.00 g of $NH_4$/ZSM-5, previously dried overnight in an oven at 110° C., was prepared and subsequently ground in an agate mortar and then calcined in air at 700° C. The heating rate was 1° C. $min^{-1}$ from room temperature up to 700° C., and the temperature was then kept at 700° C. for 0.5 h. The X-ray diffraction pattern recorded for the catalyst composition shows diffraction lines corresponding to only the starting molecular sieve.

The catalyst prepared by the above-described method was activated by different processes and the influence of the activation process was followed during the methane aromatization reaction. The different activation processes are detailed below.

Example 1

Activation under a mixture of hydrogen and n-butane (molar ratio of 9:1) from room temperature to 350° C. The catalyst was kept at this temperature for 6 h and then the reaction temperature was increased from 350 to 550° C. and held at 550° C. for 1 h under the same reactant mixture. The temperature was then increased to 700° C. under the reaction flow.

Example 2

Activation under a mixture of hydrogen and methane (molar ratio of 1:1) from room temperature to 700° C. The catalyst was kept at this temperature for 0.25 h prior to the admission of the reaction flow.

Example 3

No activation. The reaction zone containing the above-described catalyst was heated from room temperature to 700° C. directly under the reactant flow.

Figure 1:
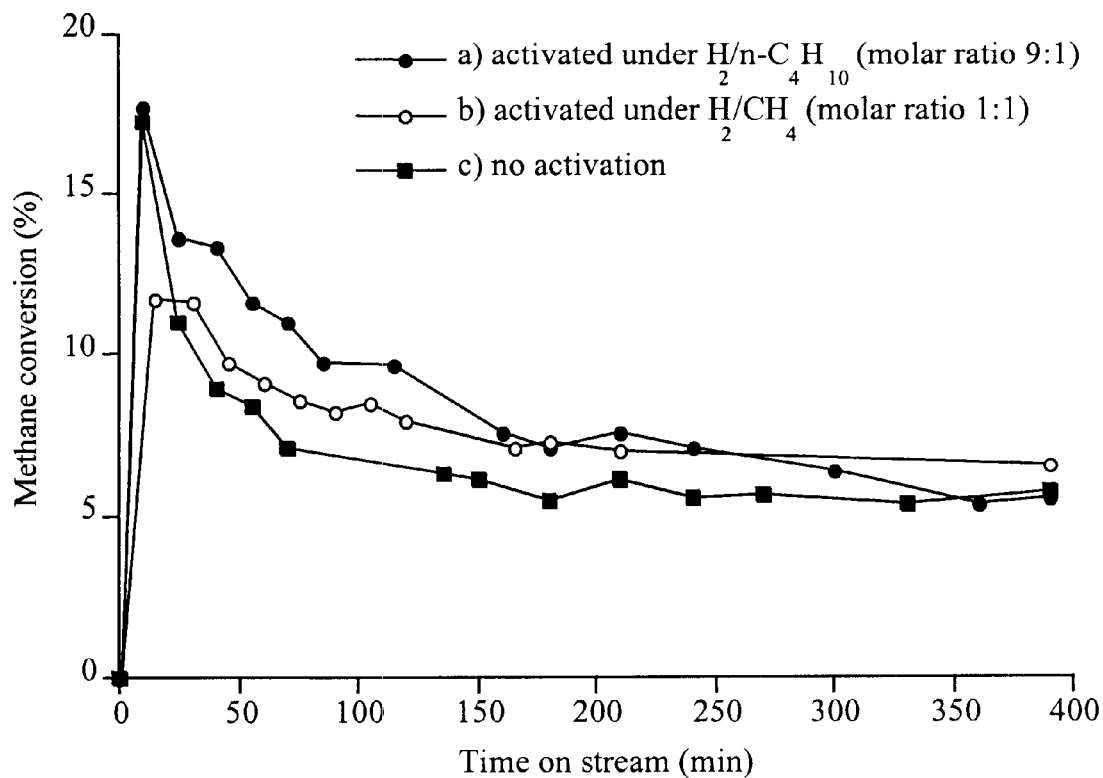
Figure 1:
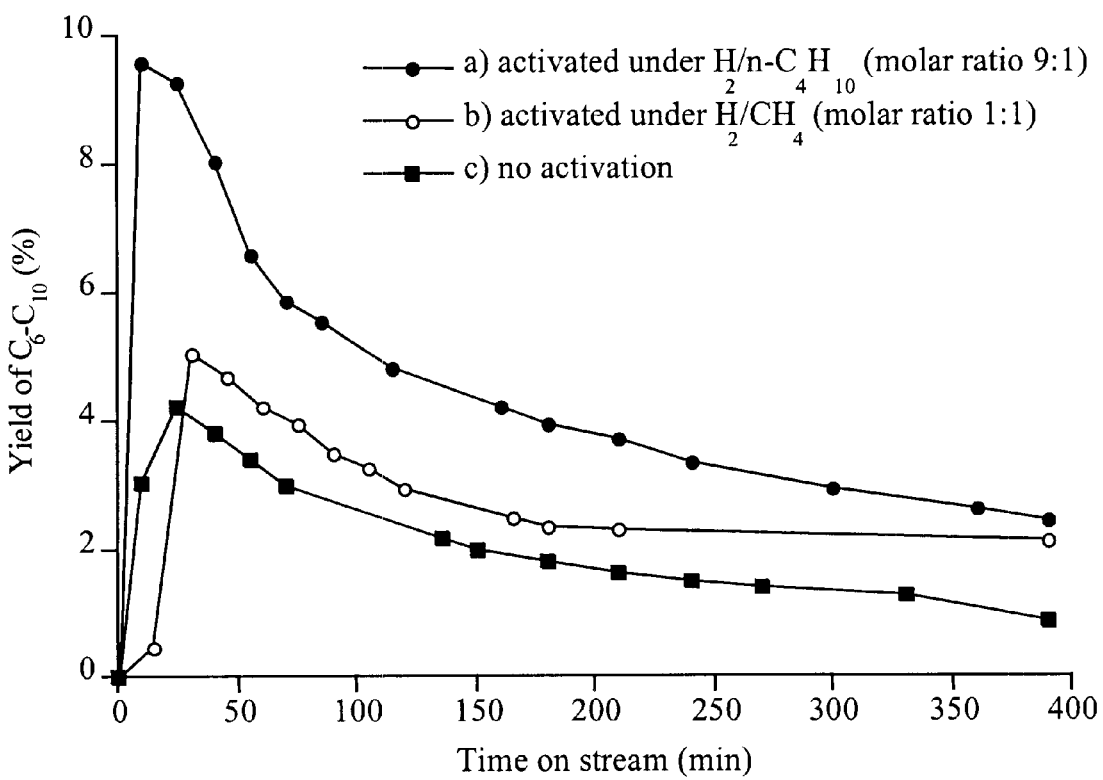

The results obtained for Examples 1–3 are presented in FIG. 1 as a function of time on stream.

Influence of Mode of Deposition of Molybdenum

In Examples 4 and 5 below, the influence of the mode of deposition of molybdenum on the crystalline aluminosilicate was studied. The amount of molybdenum was kept constant at 3.9 wt. %. Two methods of deposition were used in this example and are detailed below:

Example 4

Incipient wetness impregnation. Typically, 0.392 g of ammonium heptamolybdate salt was dissolved in 5 ml of doubly distilled water. The resulting solution was added by the incipient wetness technique to the crystalline aluminosilicate, previously dried overnight in an oven at 110° C. The impregnated crystalline material was first dried overnight in an oven at 110° C. and then subsequently calcined in air at 500° C. for 4 h. The X-ray diffraction pattern recorded for the catalyst composition shows diffraction lines corresponding only to the molecular sieve.

For each experiment, 0.50 g of the catalyst composition was activated under a mixture of hydrogen and methane (molar ratio 1:1) from room temperature to 700° C. The catalyst was kept at this temperature for 0.25 h prior to the admission of the reaction flow.

Example 5

Direct vaporization of $MoO_3$. The catalyst was prepared as in Examples 1–3 described above.

For each experiment, 0.50 g of the catalyst composition was activated under a mixture of hydrogen and methane (molar ratio 1:1) from room temperature to 700° C. The catalyst was kept at this temperature for 0.25 h prior to the admission of the reaction flow.

Figure 2:
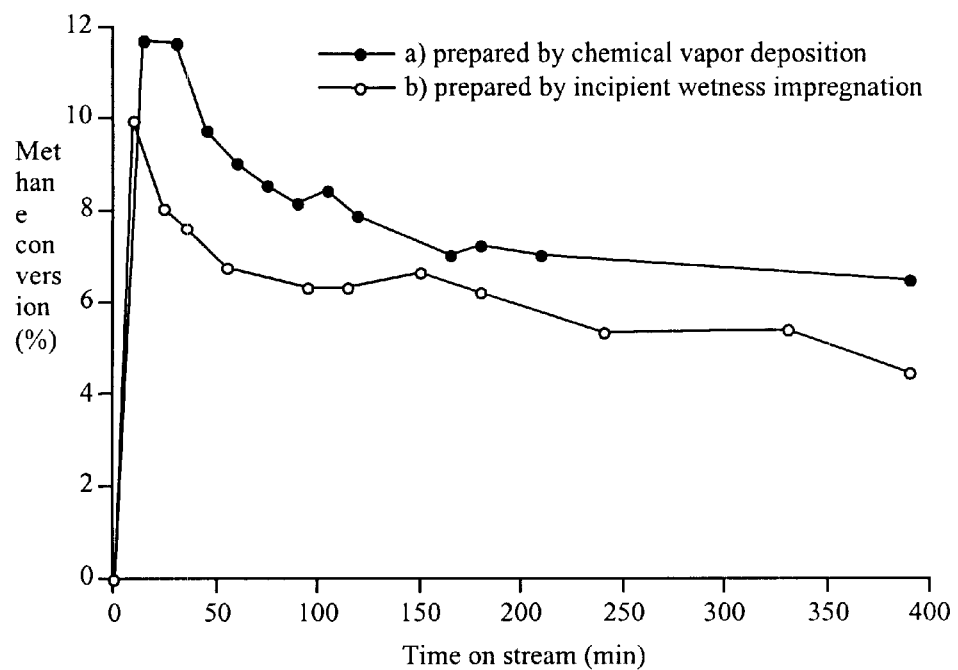
Figure 2:
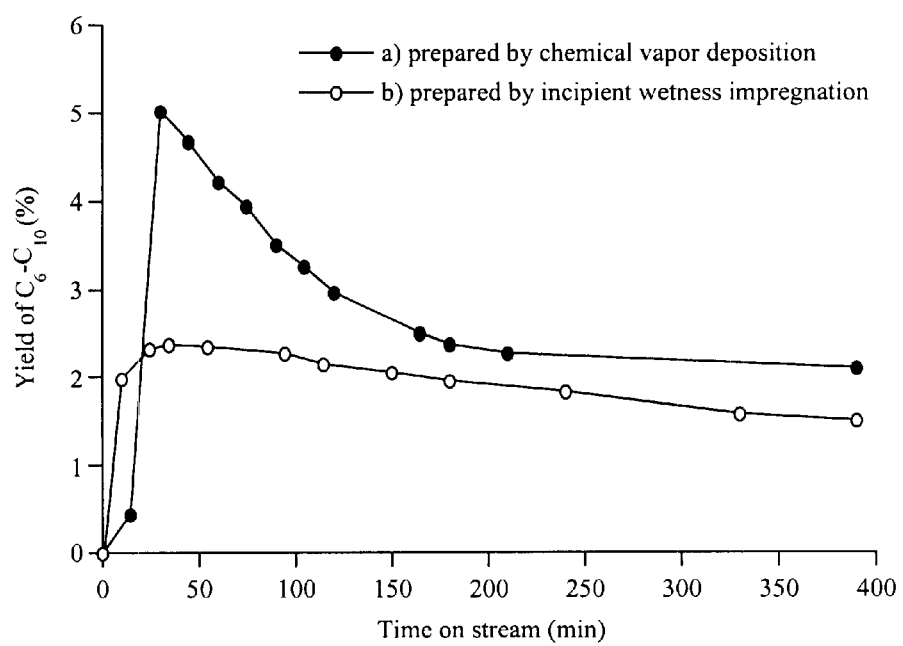

The results obtained for Examples 4–5 are presented in FIG. 2 as a function of time on stream.

Example 6

In this example, the methane aromatization process was carried out as a function of the reaction temperature from about 675° C. to about 750° C. The molybdenum concentration was kept constant at 2.1 wt. %. The catalyst composition was prepared as in Examples 1–3, with 0.15 g of $MoO_3$ and 5.00 g of $NH_4$/ZSM-5, and tested under a mixture of hydrogen and methane (molar ratio 1:1) from room temperature to the desired temperature. The catalyst was kept at this temperature for 0.25 h prior to the admission of the reaction flow.

Figure 3:
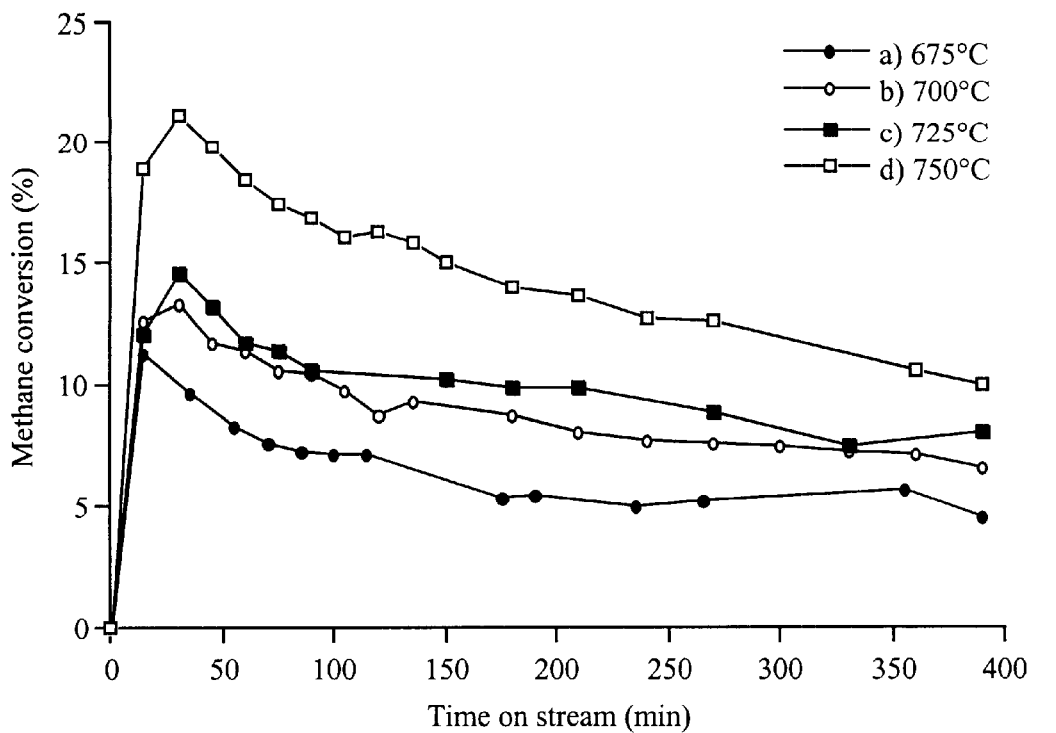
FIG. 3 is a graphical illustration of the influence of the reaction temperature on the catalytic activity of a catalyst in accordance with the present invention, over crystalline aluminosilicate supported molybdenum cluster modified with carbon and oxygen, at (a) 675° C., (b) 700° C., (c) 725° C., and (d) 750° C., and depicts the experimental results of Example 6.
Figure 3:
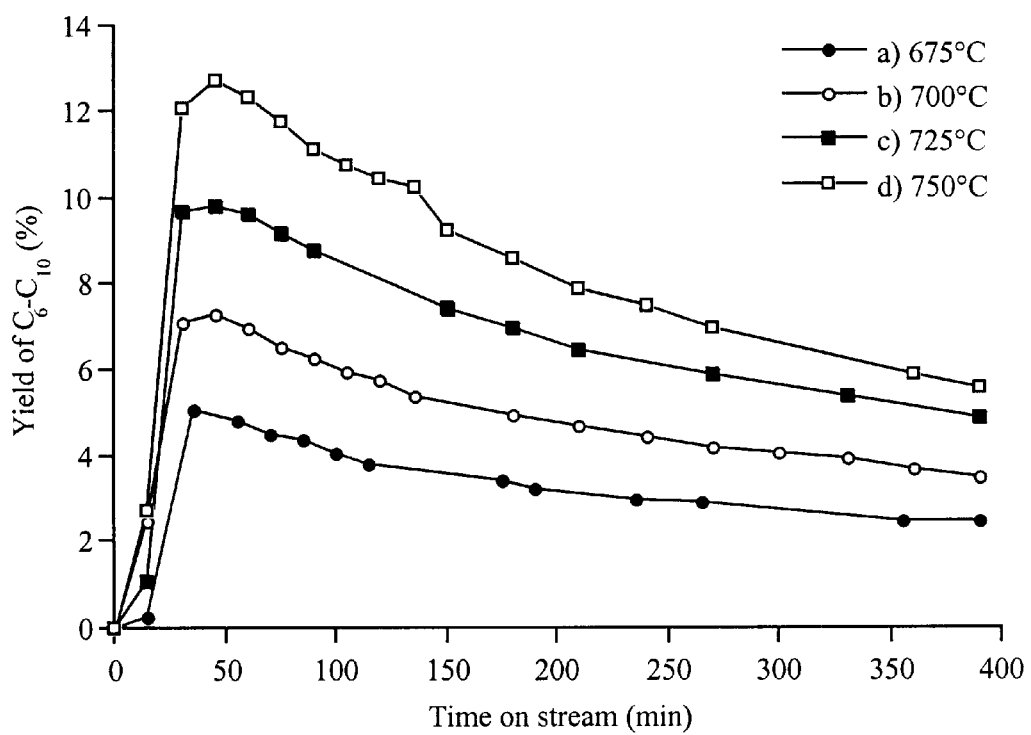

The results obtained are presented in FIG. 3 as a function of the time on stream.

Example 7

In this example, a new concept of multi-step process comprising at least two reactors in series was applied. The amount of molybdenum was kept constant at 2.1%. The catalyst composition was as in Examples 1–3, with 0.15 g of $MoO_3$ and 5.00 g of $NH_4$/ZSM-5, and was tested under a mixture of hydrogen and methane (molar ratio 1:1) from room temperature to 750° C. The catalyst was kept at this temperature for 0.25 h prior to the admission of the reaction flow. The $C_6$–$C_{10}$ products formed in the first reactor were recovered by means of an intermediate separation step, which used a cooler or cold trap containing a mixture of dry ice and acetone (−63° C.) to recover the higher hydrocarbons, and produced a reaction zone effluent stream comprising methane, helium, and hydrogen. This process allows a catalyst composition in the second reaction zone that exhibits an excellent catalyst lifetime.

Figure 4:
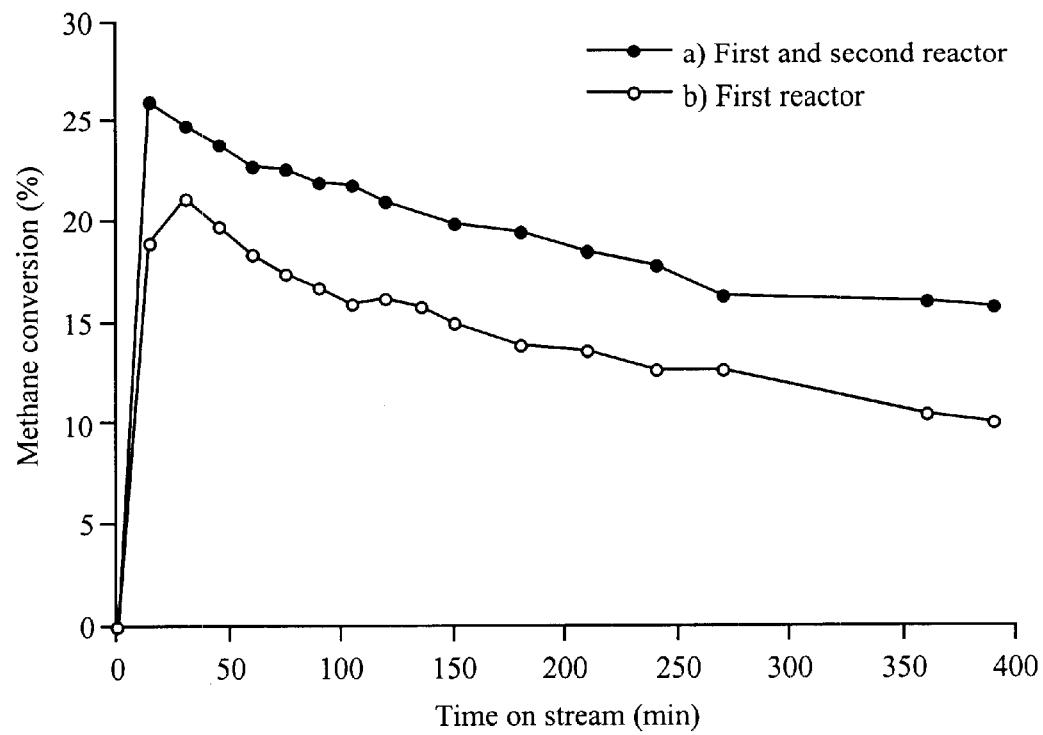
FIG. 4 is a graphical illustration of the influence of cascade reactors in accordance with the present invention on the yield of $C_6$–$C_{10}$ over crystalline aluminosilicate supported molybdenum cluster modified with carbon and oxygen at 750° C. for (a) first and second (cascade) reactor system and (b) first (single) reactor, and depicts the experimental results of Example 7.
Figure 4:
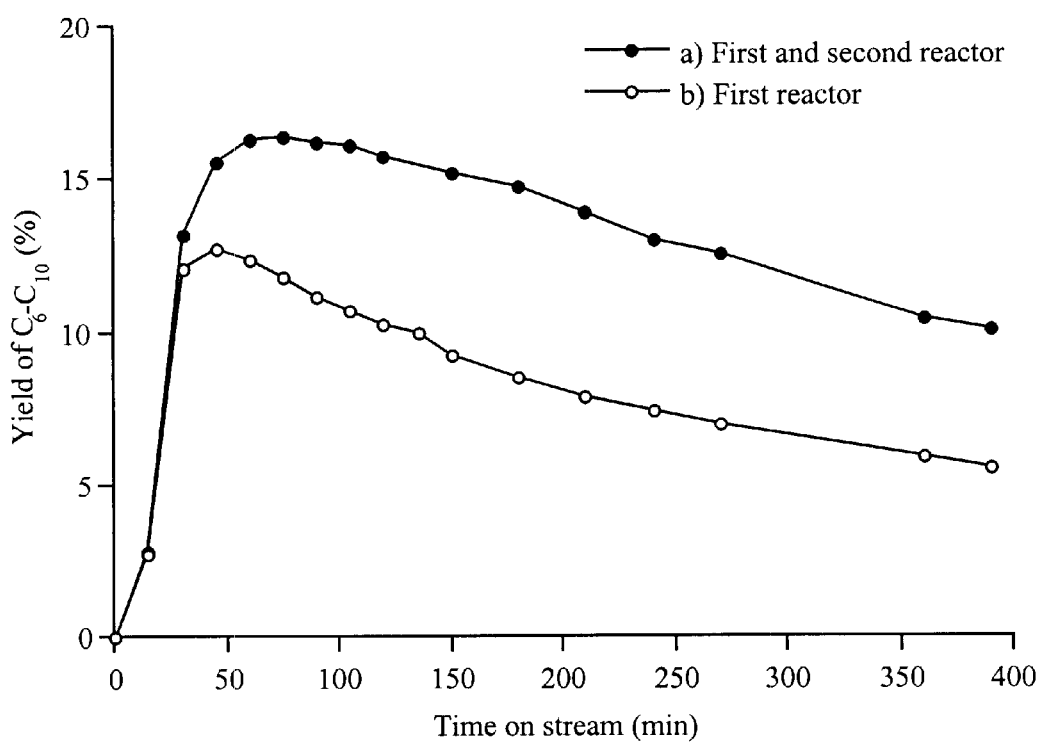

The results obtained are presented in FIG. 4 as a function of time on stream.

Example 8

In this example, a new concept of multi-step process comprising at least two reactors in series, was applied. The amount of molybdenum was kept constant at 2.1%. The catalyst was prepared as in Examples 1–3, with 0.15 g of $MoO_3$ and 5.00 g of $NH_4$/ZSM-5, and was tested under a mixture of hydrogen and methane (molar ratio 1:1) from room temperature to 700° C. The catalyst was kept at this temperature for 0.25 h prior to the admission of the reaction flow. The $C_6$–$C_{10}$ products formed in the first reactor were recovered by means of an intermediate separation step, which used a cooler containing a mixture of dry ice and acetone (−63° C.) to recover the higher hydrocarbons, and produced a reaction zone effluent stream comprising methane and hydrogen. The effluent stream was then sent through a tubular alumina membrane which comprises a vacuum reaction zone in order to remove hydrogen from the effluent stream. The process comprises passing such combined stream into this intermediate separation step allow to produce an effluent stream comprising methane and some traces of hydrogen.

The results obtained are presented in FIG. 5 as a function of time on stream.

REFERENCES

The following patents and publications, and all patents and publications referred to above, are hereby incorporated by reference for all purposes.

Y. Xu, S. Liu, L. Wang, M. Xie and X. Guo, *Cat. Letters* 30 (1995) 135–149.
F. Solymosi, A. Szõke and J. Cserenyi, *Cat. Letters* 39 (1996) 157–161.
D. Wang, J. H. Lunsford and M. P. Rosyneck, *J. Cat.* 169 (1997) 347–358.
B. M. Weckhuysen, D. Wang, M. P. Rosynek and J. H. Lunsford, *J. Cat.* 175 (1998) 338–346.
Y. Xu, S. Liu, L. Wang, M. Xie and X. Guo, *Cat. Letters* 30 (1995) 135.
F. Solymösi, A. Szöke and J. Csérenyi, *Cat. Letters* 39 (1996) 157.
L. Chen, L. Lin, Z. Xu, X. Li and T. Zhang, *J. Cat.* 157 (1995) 190.
B. M. Weckuysen, M. P. Rosynek and J. H. Lunsford, *Cat. Letters* 52 (1998) 31.
R. W. Borry III, E. C. Lu, Y. -H. Kim and E. Iglesia, *Studies in Surf. Sci. Cata.*, 119 (1998) 403.
Y. Xu, L. Lin, *Appl. Catal. A.*, 188 (1999) 53.
L. Liu, L. Wang, R. Ohnishi and M. Ichikawa, *J. Cat,* 181 (1999) 175.
J. Shu, A. Adnot and B. P. A. Grandjean, *Ind. Eng. Chem. Res.*, 38 (1999) 3860.
B. Weckuysen, D. Wang, M. P. Rosynek, J. H. Lunsford, *Proc. Int. Zeolite Conf.* 12$^{th}$ (1999), Meeting Date 1998, Volume 2, 1381–1388, M. M. J. Treacy, Editor.
L. Pierella; G. Eimer; O. Anunziata; React. Kinet. Catal. Lett. (1998), 63(2), 271–278.
L. Wang; X. Yide; S. Wong; W. Cui; X. Guo; Appl. Catal. A (1997), 152 (2), 173–182.
Dantsin, G. and Suslick, K. S., "Sonochemical Preparation of a Nanostructured Bifunctional Catalyst", *J. Am. Chem. Soc., Communications to the Editor*, Published on Web, 10.1021/ja994300w, (Received Dec. 8, 1999).
D. M. Clayson and T. K. McNiff, *European Patent Application, No* 0 228 267 A1 (1987).
J. C. Bricker, U.S. Pat. No. 5,026,937 (1991).
G. Fernand, A. Froment, W. Jozef and H. Deherrtog, U.S. Pat. No. 5,672,796 (1997).
V. Choudary, A. K. Kinage, T. Choudary; U.S. Pat. No. 5,936,135 (1999).
J. Yao; J. Kimble; C. Drake; PCT Application; WO 9903949. (1999).

We claim:

1. A process for aromatization of methane, comprising
providing a catalyst composition comprising a metal-loaded, crystalline aluminosilicate molecular sieve;
activating the catalyst composition under a combined stream comprising at least about 50 mole percent hydrocarbon and $C_2$ to $C_4$ alkanes;
contacting a feed stream comprising at least 40 mole percent methane with the catalyst composition at hydrocarbon conversion conditions comprising a temperature of from 600 to about 800° C., a pressure of less than 5 atmosphere absolute, and a Weight Hourly Space Velocity (WHSV) of 0.1–10h$^{-1}$, and
producing a reaction zone effluent stream comprising methane, hydrogen, and hydrocarbons, said hydrocarbons including at least about 30% $C_6$ to $C_{10}$ products.

2. The process of claim 1 wherein said hydrocarbons include at least about 45% $C_6$ to $C_{10}$ products.

3. The process of claim 1 wherein said hydrocarbons include at least about 60% $C_6$ to $C_{10}$ products.

4. The process of claim 1 wherein the catalyst comprises a ZSM-5 molecular sieve.

5. The process of claim 1 wherein the catalyst comprises from about 0.5 to about 4.0 wt. % molybdenum.

6. The process of claim 1 wherein the catalyst comprises a molecular sieve having a silica-to-alumina of 50:1.

7. The process of claim 1 wherein the catalyst is activated under a combined stream which comprises over about 50 mole percent hydrogen and methane.

8. The process of claim 1 wherein the catalyst composition is activated at hydrocarbon conversion conditions comprising a temperature of from about 250 to about 650° C., a pressure of less than about 5 atmospheres absolute, and a Weight Hourly Space Velocity (WHSV) of 0.5–4 h$^{-1}$.

9. The process of claim 7 wherein the feed comprises ethane.

10. The process of claim 7 wherein the feed comprises propane.

11. The process of claim 7 wherein the feed comprises butane.

12. A process for aromatization of methane, comprising introducing a feed stream comprising at least 40 mole percent methane into at least two reactors in series at hydrocarbon conversion conditions comprising a temperature of from about 600 to about 800° C., a pressure less than about 5 atmospheres absolute, and a Weight Hourly Space Velocity (WHSV) of 0.1–10 h$^{-1}$, contacting the feed stream with a catalyst composition comprising a metal-loaded crystalline aluminosilicate molecular sieve, and producing a reaction zone effluent stream comprising methane, hydrogen, and hydrocarbons, said hydrocarbons including at least about 30% $C_6$ to $C_{10}$ products,; further including the step of activating the catalyst composition under a combined stream comprising at least 50 mole percent hydrogen and $C_2$ to $C_4$ alkanes.

13. The process of claim 12 further including the step of treating an intermediate stream between two of said reactor in series so as to remove $C_6$ to $C_{10}$ products from said intermediate stream.

14. The process of claim 13 further including the step of treating an intermediate stream between two of said reactor in series so as to remove hydrogen from said intermediate stream.

15. The process of claim 13 wherein said hydrocarbons include at least about 45% $C_6$ to $C_{10}$ products.

16. The process of claim 13 wherein said hydrocarbons include at least about 60% $C_6$ to $C_{10}$ products.

17. The process of claim 13 wherein the catalyst comprises a ZSM-5 molecular sieve.

18. The process of claim 13 wherein the catalyst comprises from about 0.5 to about 4.0 wt. % molybdenum.

19. The process of claim 13 wherein the catalyst comprises a molecular sieve having a silica-to-alumina ratio of about 50:1.

20. The process of claim 12 wherein the catalyst is activated under a combined stream comprising more than about 50 mole percent of hydrogen and methane.

21. The process of claim 12 wherein the catalyst is activated at hydrocarbon conversion conditions comprising a temperature of from about 250 to about 650° C., a pressure of less than about 5 atmospheres absolute, and a Weight Hourly Space Velocity (WHSV) of 0.5–4 h$^{-1}$.

22. The process of claim 13 wherein the effluent stream is passed to an intermediate separator comprising a hydrogen transport alumina modified membrane with a vacuum reaction zone.

23. A process for aromatization of methane, comprising:

contacting a feed stream comprising at least 40 mole percent methane with a catalyst composition at hydrocarbon conversion conditions comprising a temperature of from about 600 to about 800° C., a pressure of less than 5 atmospheres absolute, and a Weight Hourly Space Velocity (WHSV) of 0.1–10h$^{-1}$, wherein the catalyst comprises:

a ZSM-5 molecular sieve having a silica-to-alumina ratio of 50:1; and from about 0.5 to about 4.0 wt. % molybdenum; and producing a reaction zone effluent stream comprising methane, hydrogen, hydrocarbons, said hydrocarbons including at least about 30% $C_6$ to $C_{10}$ products; further including the step of activating the catalyst composition under a combined stream comprising at least about 50 mole percent hydrogen and $C_2$ to $C_4$ alkanes prior to the contacting the catalyst composition with the feed stream.

* * * * *